United States Patent
Reynolds et al.

(10) Patent No.: US 6,379,352 B1
(45) Date of Patent: *Apr. 30, 2002

(54) LARGE SURFACE CARDIAC ABLATION CATHERTER THAT ASSUMES A LOW PROFILE DURING INTRODUCTION INTO THE HEART

(75) Inventors: Jeffrey N. Reynolds, Santa Clara; Thomas Bourne, Mountain View; Jerome Jackson, Sunnyvale; Gloria Alvarez, Tracy; Stuart D. Edwards, Los Altos, all of CA (US)

(73) Assignee: EP Technologies, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/533,023

(22) Filed: Mar. 22, 2000

(Under 37 CFR 1.47)

Related U.S. Application Data

(63) Continuation of application No. 08/099,994, filed on Jul. 30, 1993, now Pat. No. 6,086,581, which is a continuation-in-part of application No. 07/951,728, filed on Sep. 25, 1992, now Pat. No. 5,471,982.

(51) Int. Cl.[7] .......................... A61B 18/14; A61B 5/042; A61N 1/05
(52) U.S. Cl. ........................... 606/41; 600/374; 607/99
(58) Field of Search .................... 606/41; 600/374; 607/98, 99, 122, 126

(56) References Cited

U.S. PATENT DOCUMENTS

| | | | |
|---|---|---|---|
| 3,326,207 A | * 6/1967 | Egan | |
| 3,435,826 A | 4/1969 | Fogarty | ............. 606/194 |
| 3,448,739 A | 6/1969 | Stark et al. | ............. 604/103 |
| 4,444,195 A | * 4/1984 | Gold | |
| 4,522,212 A | * 6/1985 | Gelinas et al. | |
| 4,573,473 A | * 3/1986 | Hess | |
| 4,628,937 A | * 12/1986 | Hess et al. | |
| 4,630,611 A | * 12/1986 | King | |
| 4,641,649 A | * 2/1987 | Walinsky et al. | |
| 4,649,924 A | * 3/1987 | Taccardi | |
| 4,660,571 A | * 4/1987 | Hess et al. | |
| 4,662,383 A | 5/1987 | Sogawa et al. | |
| 4,664,120 A | * 5/1987 | Hess | |
| 4,676,258 A | 6/1987 | Inokuchi et al. | |
| 4,681,117 A | * 7/1987 | Brodman et al. | |
| 4,690,148 A | * 9/1987 | Hess | |
| 4,690,155 A | * 9/1987 | Hess | |
| 4,699,147 A | * 10/1987 | Chilson et al. | |
| 4,784,133 A | * 11/1988 | Mackin | |
| 4,862,887 A | * 9/1989 | Weber et al. | |

(List continued on next page.)

FOREIGN PATENT DOCUMENTS

| | | | |
|---|---|---|---|
| DE | 35116830 | 11/1986 | ............. 607/99 |
| GB | 2077596 | 12/1981 | ............. 128/642 |
| GB | 2163055 | 2/1986 | ............. 128/642 |
| SU | 1220673 | 3/1986 | ............. 607/126 |
| WO | 8906148 | 7/1989 | ............. 607/126 |
| WO | WO95/01751 | 1/1995 | |

OTHER PUBLICATIONS

Schaudinischky et al; "The Shape Conforming Electrode", Med. & Biol. Eng., vol. 7, pp. 341–343. 1969.

Primary Examiner—Lee Cohen
(74) Attorney, Agent, or Firm—Lyon & Lyon LLP

(57) ABSTRACT

A cardiac ablation catheter has an energy emitting surface for thermally destroying tissue. The surface normally presents a compact, low profile for introduction into the heart. Once introduced, the energy emitting surface can be significantly enlarged. The enlarged surface emits ablation energy sufficient to create a lesion that is significantly larger in terms of volume and geometry than the surface's initial low profile would provide.

11 Claims, 3 Drawing Sheets

U.S. PATENT DOCUMENTS

| | | | |
|---|---|---|---|
| 4,882,777 A | * | 11/1989 | Narula |
| 4,890,623 A | * | 1/1990 | Cook et al. |
| 4,891,102 A | * | 1/1990 | Astrinsky et al. |
| 4,928,695 A | * | 5/1990 | Goldman et al. |
| 4,940,064 A | * | 7/1990 | Desai et al. |
| 4,944,088 A | * | 7/1990 | Doan et al. |
| 4,945,912 A | * | 8/1990 | Langberg |
| 4,952,357 A | | 8/1990 | Euteneuer |
| 4,955,377 A | | 9/1990 | Lennox et al. |
| 4,974,162 A | | 11/1990 | Siegel et al. |
| 4,976,710 A | | 12/1990 | Mackin |
| 4,976,711 A | | 12/1990 | Parins et al. |
| 4,979,510 A | | 12/1990 | Franz et al. |
| 4,979,948 A | | 12/1990 | Geddes et al. |
| 5,003,991 A | | 4/1991 | Takayama et al. |
| 5,006,119 A | | 4/1991 | Acker et al. |
| 5,025,786 A | | 6/1991 | Siegel |
| 5,029,585 A | | 7/1991 | Lieber et al. |
| 5,041,973 A | | 8/1991 | Lebron et al. |
| 5,045,056 A | | 9/1991 | Behl |
| 5,056,517 A | | 10/1991 | Fenici |
| 5,084,044 A | | 1/1992 | Quint |
| 5,114,423 A | | 5/1992 | Kasprzyk et al. |
| 5,150,717 A | | 9/1992 | Rosen et al. |
| 5,156,151 A | | 10/1992 | Imran |
| 5,195,968 A | | 3/1993 | Lundquist |
| 5,228,442 A | | 7/1993 | Imran ........................ 128/642 |
| 5,255,678 A | | 10/1993 | Deslauriers et al. ........ 128/642 |
| 5,255,679 A | | 10/1993 | Imran |
| 5,263,493 A | | 11/1993 | Avitall |
| 5,277,201 A | | 1/1994 | Stern .......................... 607/98 |
| 5,282,845 A | | 2/1994 | Bush et al. |
| 5,311,866 A | | 5/1994 | Kagan et al. |
| 5,324,968 A | | 6/1994 | Imran |
| 5,345,936 A | | 9/1994 | Pomeranz et al. ...... 607/122 X |
| 5,575,772 A | | 11/1996 | Lennox |
| 5,588,432 A | | 12/1996 | Crowley |
| 5,860,974 A | * | 1/1999 | Abele .......................... 606/41 |
| 6,086,581 A | * | 7/2000 | Reynolds et al. ............. 606/41 |

\* cited by examiner

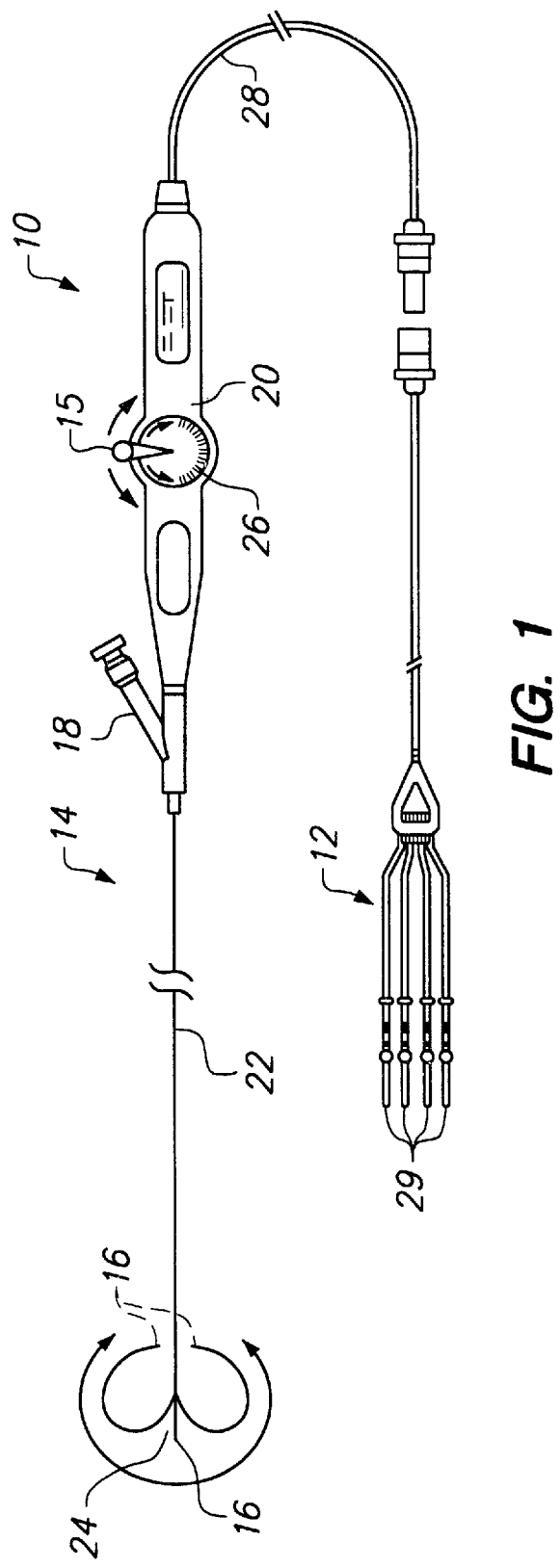
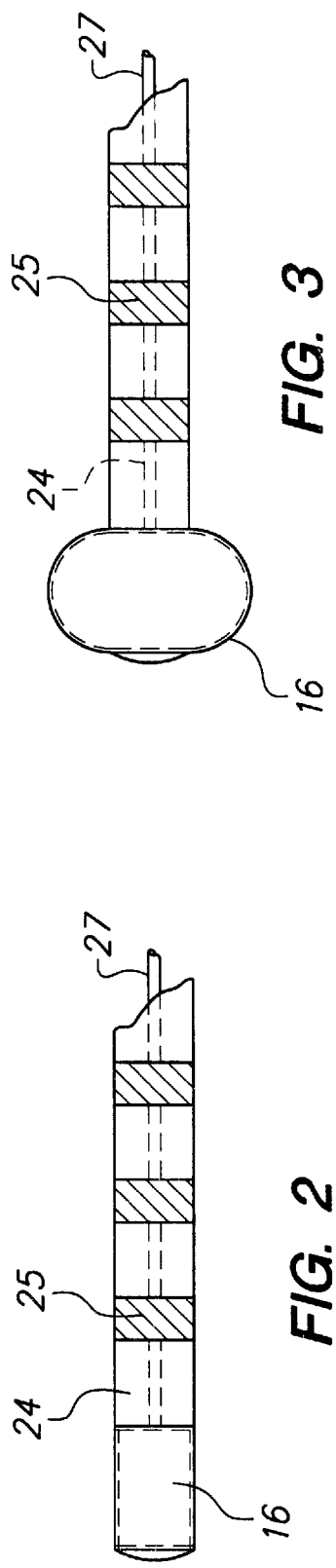
FIG. 1
FIG. 2
FIG. 3

LARGE SURFACE CARDIAC ABLATION CATHERTER THAT ASSUMES A LOW PROFILE DURING INTRODUCTION INTO THE HEART

RELATED APPLICATION

This application is a continuation of U.S. application Ser. No. 08/099,994, filed on Jul. 30, 1993, now U.S. Pat. No. 6,086,581, which is a continuation-in-part of U.S. application Ser. No. 07/951,728, filed Sep. 25, 1992, now U.S. Pat. No. 5,471,982, and entitled "Cardiac Mapping and Ablation Systems."

FIELD OF THE INVENTION

The invention relates to systems and methods for ablating the interior regions of the heart for treating cardiac conditions.

BACKGROUND OF THE INVENTION

It is believed that lesions larger than those created by current electrophysiological therapy are needed to more consistently cure myocardial ventricular tachycardia (MVT) of ischemic origins.

Conventional cardiac ablation systems designed to cure re-entrant supra ventricular tachycardia (SVT), often create lesions in myocardial tissue with a penetration depth of about 3 to 5 mm and a lesion volume of less than 0.2 $cm^3$, depending upon the size of the electrode and the amount of power that is applied.

However, to consistently cure MVT by ablation, a penetration depth greater than 3 to 5 mm and a lesion volume of at least 1 $cm^3$ is estimated to be required.

The solution lies in larger electrodes. Yet, larger electrodes themselves pose problems of size and maneuverability that weigh against safe and easy introduction through a vein or artery into the heart.

A need exists for cardiac ablation catheters having that flexibility and maneuverability that permits safe and easy introduction into the heart and, once deployed inside the heart, emit energy sufficient to cause permanent, irreversible thermal damage to large regions of myocardial tissue.

SUMMARY OF THE INVENTION

The invention provides a cardiac ablation catheter having an energy emitting surface for thermally destroying tissue. The surface normally presents a compact, low profile for introduction into the heart.

Once introduced, the energy emitting surface can be significantly enlarged. The enlarged surface emits ablation energy sufficient to create a lesion that is significantly larger in terms of volume and geometry than the surface's initial low profile would provide.

The catheter of this invention is configured to produce lesions with a greater surface area, compared to standard cardiac ablation catheters, while maintaining a standard (6, 7, or 8 French) introducer size (a "French" equals 0.013 inches).

The enlarged surface area creates larger lesions, since the lesion volume and geometry are factors which are controlled according to the shape and size of the energy emitting surface.

In accordance with a further aspect of the invention, an inflatable surface is produced using a thermoplastic polymeric material such as polyethylene. The inflatable surface is coated, all or partially, with an energy emitting material. When deflated, such a surface presents a compact profile. When inflated, the same surface has an significantly enlarged dimension of, for example, approximately 7 to 12 mm.

Another aspect of the invention is an expandable energy emitting surface with an associated temperature sensor.

In an alternative arrangement, the expandable surface can also be used for obtaining electrogram recordings or for similar mapping procedures.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

BRIEF DESCRIPTION OF DRAWINGS

FIG. 1 is a plan view with parts broken away showing an ablation catheter system of the present invention;

FIG. 2 is a greatly magnified broken-away plan view of a tip portion of an electrode in accordance with the invention;

FIG. 3 is a view of the enlarged fragmentary tip portion, shown in FIG. 2, with an electrode shown in the expanded condition;

DETAILED DESCRIPTION

Figure 4:
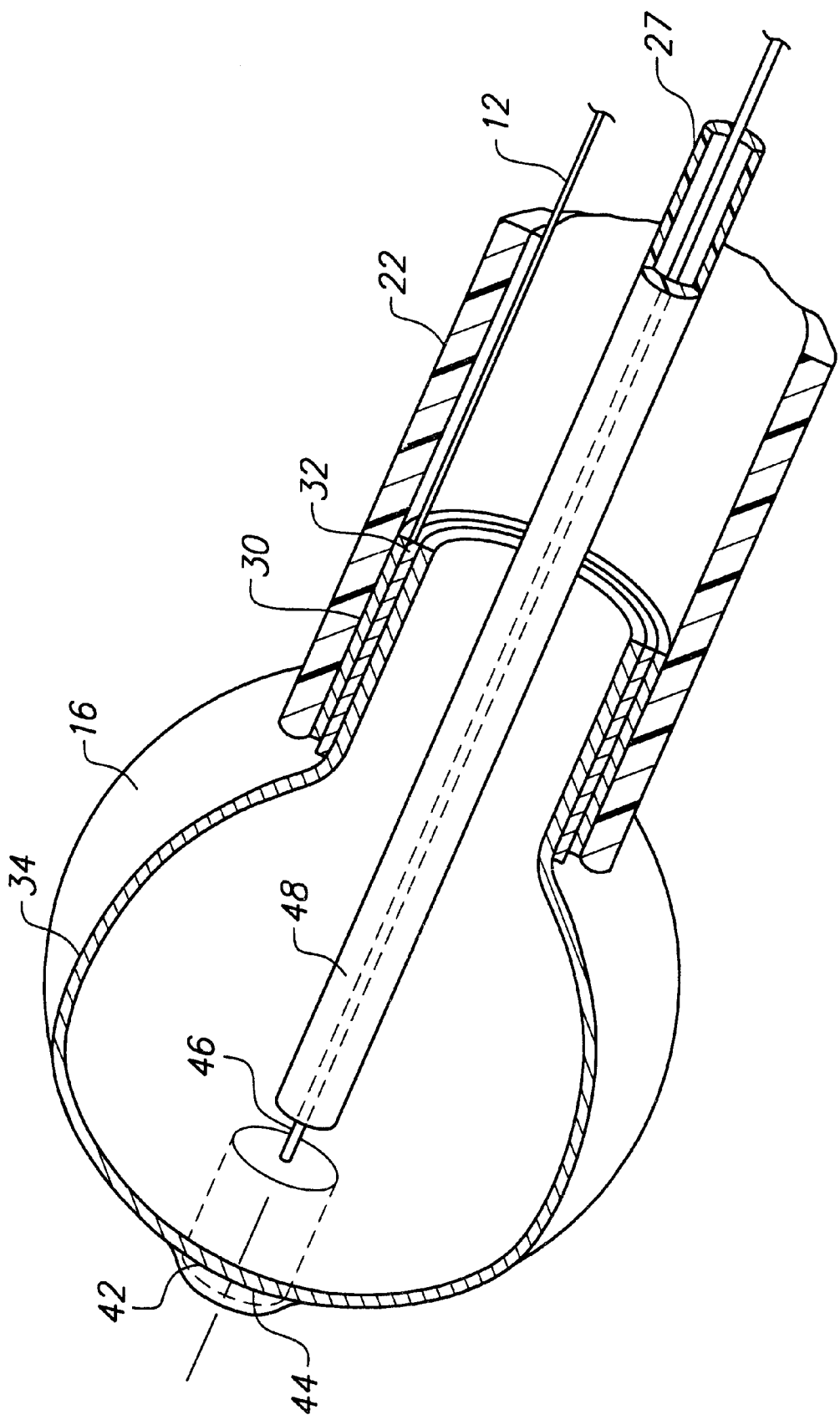
FIG. 4 is a yet, more greatly enlarged fragmentary view of the tip portion of an electrode of the present invention with parts shown in cross-section for clarity.

FIG. 1 shows a system 10 for performing ablation on cardiac tissue that embodies the features of the invention.

The system 10 also includes a steerable catheter 14 carrying an expandable energy emitting body 16.

In FIG. 1, the catheter 14 includes a handle 20, a guide tube 22, and a distal tip 24. In this embodiment, the tip 24 carries the energy emitting body 16 (see FIG. 2).

As FIG. 2 shows, a series of ring electrodes 25 encircle the guide tube 22 close to the energy emitting body 16. These ring electrodes 25 can be used for sensing electrograms to locate the region that is to be ablated.

The handle 20 encloses a steering mechanism 26 for the catheter tip 24. A cable 28 extending from the rear of the handle 20 has plugs 29 which connect the catheter 14 to a source of ablation energy. The ablation energy is conveyed through the wires 12 to the body 16 for creating lesions in tissue within the heart.

While the type of ablation energy used can vary, in the illustrated embodiment (see FIG. 5), radio frequency (RF) electromagnetic energy is used. The energy source therefore comprises a radio frequency 50. While the RF 50 can be constructed in various ways, the RF generator preferably delivers up to about 150 watts of power at a frequency of about 350 to 700 kHz, and most preferably, about 500 kHz.

Left and right steering wires (not shown) extend through the guide tube 22 to interconnect the steering mechanism 26 with the distal tip 24. The steering mechanism 26 includes a steering lever 15.

Various steering mechanisms can be used, for example, the type shown in U.S. Pat. No. 5,195,968.

As FIG. 1 shows, rotation of the steering lever 15 to the left pulls on the left steering wire, causing the tip 24 to bend to the left. Rotation of the steering lever 15 to the right pulls on the right steering wire, causing the tip 24 to bend to the right.

As FIG. 1 also shows, the energy emitting body 16 moves along with the tip 24 from left and right as the steering lever 15 is manipulated.

In use, a physician holds the catheter handle 20 and introduces the catheter 14 through a main vein or artery (typically the femoral) into the interior region of the heart that is to be treated. The physician then further steers the distal tip of the catheter 14 by means of the steering lever 15, to place the body 16 into contact with the tissue within the heart that is targeted for ablation.

The body 16 has a hollow interior. The guide tube 22 includes an interior lumen 27 (see FIG. 2) that communicates with the hollow interior of the body 16.

The catheter assembly 10 includes an injection port 18 for injection of a fluid medium into the lumen 27. The fluid caused the body 16 to expand or inflate from its normal, low profile condition (as FIG. 2 shows) to an enlarged operating condition (as FIG. 3 shows).

The inflating fluid medium can vary. Preferably, it comprises a liquid like as water, saline solution, or other biocompatible fluid.

Alternately the inflating fluid medium can comprise a gaseous medium such as carbon dioxide or air.

Regardless of the type of fluid medium, the inflation preferably occurs under relatively low pressures of up to 30 psi. The pressure used depends upon the desired rate of inflation, the strength and material used for the body 16, and the degree of flexibility required (i.e., high pressure leads to a harder, less flexible body 16.

After reaching its desired inflated condition, the physician directs ablation energy through wires 12 into the body 16. The body emits the ablation energy to heats the tissue. The tissue is thermally destroyed, forming a lesion.

The body 16 can be variously constructed. In the illustrated and preferred embodiment, the body 16 is made of a thermoplastic polymeric material of a pliant nature, like polyethylene. The body 16 is formed by either a free-blown process or a mold process.

The body 16 includes an energy emitting coating applied upon its exterior surface. In the illustrated embodiment, where the body 16 emits RF ablation energy, the coating comprises an electrically conducting material, like platinum or gold.

Coating of the body 16 may be accomplished by conventional painting or sputter coating techniques. For example, gold can be sputtered onto the exterior surface of the body 16. Alternatively, a two phase sputter coating process may be employed in which an initial layer of titanium is applied followed by an outer coating of gold.

The coating process may also use an ion beam assisted deposition (IBAD) process. This process implants the conductive material into the polymer of the body 16.

The wires 12 conduct ablating energy to the coating on the body 16.

Figure 5:
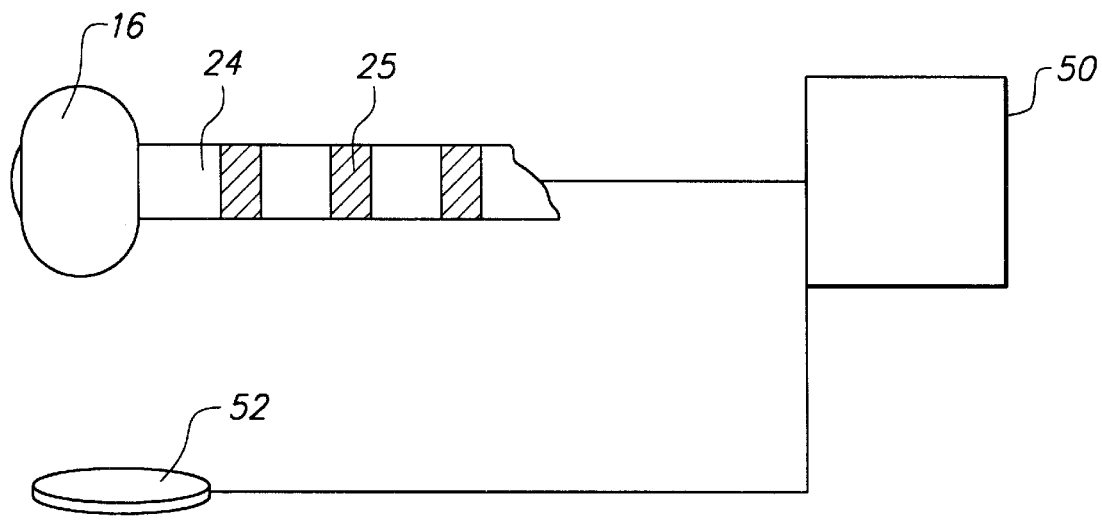
FIG. 5 shows a diagrammatic view of the cardiac ablation system shown in FIG. 3 coupled to a source of radio frequency electromagnetic energy and an indifferent electrode for electrically heating and ablating myocardial tissue.

The body 16 shown in FIGS. 2, 3 and 5 is operated in a unipolar ablation mode. The energy transmitted by the body 16 flows through myocardial tissue to an external indifferent electrode 52 on the patient (see FIG. 5), which is typically an epidermal patch.

In the illustrated and preferred embodiment, the conductive coating covers the entire exposed area of the body 16. In this case, the body 16, when inflated, functions as a single ablation electrode.

Figure 6:
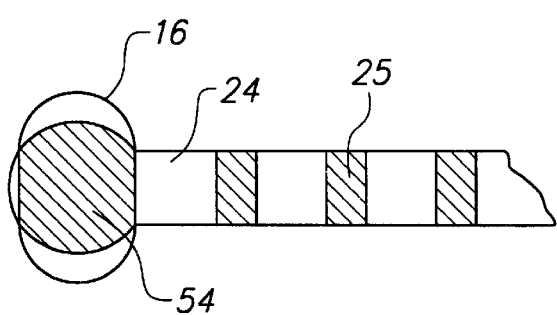
FIG. 6 is a view of the enlarged fragmentary tip portion, as shown in FIG. 3, with the conductive coating applied in a pattern.

Alternatively, the conductive coating can be applied in a defined portion 54 (such as one third or one half) of the circumference of the body 16 (as shown in FIG. 6), or any variety of patterns that may enhance the ablation performance and/or optimize the ablation procedure.

Additionally, the coated, inflatable body 16 can serve to carry electrical signals from the heart tissue along wires 12 through cable 28 and plugs 29 for recording of electrogram potentials by recording equipment.

The inflatable body 16 can be attached to the distal tip 24 of guide tube 22 in various ways.

In the illustrated embodiment, as best seen in FIG. 4, the distal end of guide tube 22 is adhered over a high resistivity layer 30 of a polymer, such as an epoxy resin. The layer 30, in turn, overlies a conductive ring 32.

The distal end of the signal wire 12 is attached to conductive ring 32, which is conductively connected to the outer electrically conductive coating 34 on the outer surface of tip 16, preferably using a highly conductive material, like epoxy resin.

In this arrangement, the inflation lumen 27 forms a fluid pressure transmitting conduit which communicates with the interior of body 16. The lumen 27 extends from the injection port 18 through the bore 25 of the guide tube 22 to the distal tip 24.

The physician has the option to maneuver the distal catheter tip 24 toward the desired endocardial location. The physician may inflate the body 16 whenever the physiology and safety of the patient allows, either within the heart or while in transit toward the heart, by conducting positive fluid pressure through the lumen 27 to the inflatable body 16.

The positive fluid pressure causes the body 16 to expand or inflate. The inflating body 16 deploys outward, assuming a prescribed three dimension shape. The shape can vary, depending upon the premolded configuration of the body 16. In the illustrated embodiment, the body 16 assumes a somewhat spherical shape when inflated.

The inflation is conducted to the extent that the body 16 is filled and expanded, but not stretched. The electrical conductivity of the coating on the body 16 is thus not disturbed or impaired.

Due to its pliant nature, the body 16, when inflated, naturally conforms to the topography of the endocardial surface next to it.

Release of the positive fluid pressure and the application of negative pressure through the supply conduit will drain fluid from the body 16. The body 16 collapses back into a deflated condition and, depending on the specific catheter design, may be retracted back into the catheter.

Alternatively, a movable sheath controlled by a retraction mechanism can be used to selectively enclose the body 16 before and after use, during insertion into and retraction from the body. The retraction mechanism is retracted to free the body 16 for inflation and use.

The body 16 can be carried on existing catheter assemblies. When in its normal, low profile condition, shown in FIG. 1, the body 16 maintains a standard 6, 7, or 8 French size. When in its inflated condition, shown in FIG. 2, the same body 16 has an significantly enlarged dimension ranging from approximately 7 mm to 12 mm.

In the illustrated and preferred embodiment (see FIG. 4), the system 10 includes monitoring means 42 for sensing the temperature.

While the monitoring means 42 may be variously constructed, in the illustrated embodiment, it temperature sensing means 44 associated with the body 16. The means 44 includes a small bead thermistor with associated lead wires 46 that pass through the interior of the body 16. A sheath 48 provides a protective conduit for the lead wires 46. The wires 46 extend back to the handle 20 for electrical connection to cable 28.

Preferably, the system 10 also includes control means (not shown) for the energy power supply that is responsive to the sensed temperature for performing generator control functions.

What is claimed is:

1. A tissue ablating catheter, comprising:
   an elongated guide member having a cross sectional dimension;
   a body carried by the guide member having an exterior surface with a normal cross sectional dimension no greater than the cross sectional dimension of the guide member and inflatable from its normal cross sectional dimension to a second cross sectional dimension greater than the cross sectional dimension of the guide member; and
   an electrically conductive coating on the exterior surface of the body to transmit RF ablating energy from the body sufficient to cause permanent, irreversible thermal damage to body tissue.

2. The catheter of claim 1, further including a temperature sensing device associated with the body.

3. The catheter of claim 1, wherein the body is formed of a polymer material.

4. The catheter of claim 1, further including an element to deflect the guide member to position the body.

5. The catheter of claim 1, wherein the guide member includes a layer of high resistivity material sandwiched between the guide member and the electrically conductive coating to attach the body to the guide member.

6. The catheter of claim 1, wherein the coating covers the entire body.

7. The catheter of claim 1, wherein the coating comprises a pattern applied to the body.

8. The catheter of claim 1, wherein the catheter is a cardiac ablating catheter and the electrically conductive coating carries electrical signals from myocardial tissue to map electrical activity in myocardial tissue.

9. A cardiac ablating catheter, comprising:
   an elongated guide member having a cross sectional dimension;
   a body carried by the guide member having an exterior surface with a normal cross sectional dimension no greater than the cross sectional dimension of the guide member and inflatable from its normal cross sectional dimension to a second cross sectional dimension greater than the cross sectional dimension of the guide member; and
   an electrically conductive coating on the exterior surface of the body to carry electrical signals from myocardial tissue to map electrical activity in myocardial tissue and to transmit RF ablating energy from the body sufficient to cause permanent, irreversible thermal damage to myocardial tissue.

10. A tissue ablating catheter, comprising:
    an elongated guide member having a cross sectional dimension;
    a body carried by the guide member having an exterior surface with a normal cross sectional dimension no greater than the cross sectional dimension of the guide member and inflatable from its normal cross sectional dimension to a second cross sectional dimension greater than the cross sectional dimension of the guide member;
    an electrically conductive coating on the exterior surface of the body to transmit RF ablating energy from the body sufficient to cause permanent, irreversible thermal damage to body tissue;
    a layer of electrically conductive material overlying a portion of the electrically conductive coating; and
    a wire electrically connected to the electrically conductive layer to conduct ablating energy to the electrically conductive coating.

11. The catheter of claim 10, wherein the guide member includes a layer of high resistivity material sandwiched between the guide member and the electrically conductive coating to attach the body to the guide member.

* * * * *